(12) United States Patent
Van Pee et al.

(10) Patent No.: US 12,263,008 B2
(45) Date of Patent: Apr. 1, 2025

(54) APPARATUS, SYSTEM AND METHOD FOR DIAGNOSING SLEEP

(71) Applicant: Ectosense NV, Rotselaar (BE)

(72) Inventors: Bart Van Pee, Leuven (BE); Frederik Massie, Leuven (BE); Duarte Mingot De Almeida Mendes De Almeida, Lisbon (PT)

(73) Assignee: Ectosense NV (BE)

( * ) Notice: Subject to any disclaimer, the term of this patent is extended or adjusted under 35 U.S.C. 154(b) by 866 days.

(21) Appl. No.: 16/507,405

(22) Filed: Jul. 10, 2019

(65) Prior Publication Data

US 2020/0015737 A1    Jan. 16, 2020

(30) Foreign Application Priority Data

Jul. 11, 2018   (EP) ..................... 18182957

(51) Int. Cl.
  *A61B 5/00*   (2006.01)
  *A61B 5/02*   (2006.01)
  *A61B 5/024*  (2006.01)

(52) U.S. Cl.
  CPC .......... *A61B 5/4818* (2013.01); *A61B 5/0002* (2013.01); *A61B 5/02007* (2013.01); *A61B 5/02427* (2013.01); *A61B 5/6832* (2013.01)

(58) Field of Classification Search
  CPC .............. A61B 5/4818; A61B 5/02007; A61B 5/02427; A61B 5/6832; A61B 5/0002
  See application file for complete search history.

(56) References Cited

U.S. PATENT DOCUMENTS 6,319,205 B1 * 11/2001 Goor ................... A61B 5/6806
                                                  600/483
6,856,829 B2 *  2/2005 Ohsaki ............... A61B 5/02416
                                                  600/479

(Continued)

FOREIGN PATENT DOCUMENTS

EP         0926980 B1    10/2008
JP       2004220834 A  *  8/2004  ............... G01J 1/32

(Continued)

OTHER PUBLICATIONS

Peper, Erik et al. (2007). Is There More to Blood Volume Pulse Than Heart Rate Variability, Respiratory Sinus Arrhythmia, and Cardiorespiratory Synchrony ?. Biofeedback. 35. 54-61 (Year: 2007).*

(Continued)

*Primary Examiner* — Ashley K Buran
*Assistant Examiner* — Helene Bor
(74) *Attorney, Agent, or Firm* — Botos Churchill IP Law LLP

(57) ABSTRACT

A system is configured to diagnose sleep comprising an apparatus configured to be attached to a patient; the apparatus comprises: i) an optical sensor configured to measure a blood volume pulse of the patient; and ii) a wireless communication interface configured to wirelessly transmit the measured blood volume pulse. The system further comprises means for performing: i) obtaining the wirelessly transmitted measured blood volume pulse; and ii) deriving from the blood volume pulse the peripheral arterial tone; iii) determining occurrences of sleep events from changes in the peripheral arterial tone.

21 Claims, 6 Drawing Sheets

(56) References Cited

U.S. PATENT DOCUMENTS

| | | | |
|---|---|---|---|
| 7,024,234 B2 | 4/2006 | Margulies et al. | |
| 10,632,009 B2* | 4/2020 | Goff | A61B 5/68335 |
| 2005/0004423 A1* | 1/2005 | Shenosky | A61G 10/005 |
| | | | 600/21 |
| 2006/0009700 A1* | 1/2006 | Brumfield | A61B 5/6838 |
| | | | 600/587 |
| 2010/0240982 A1* | 9/2010 | Westbrook | A61B 5/4818 |
| | | | 600/538 |
| 2013/0237775 A1* | 9/2013 | Gross | G16H 40/63 |
| | | | 600/301 |
| 2016/0213309 A1* | 7/2016 | Sannholm | A61B 5/7271 |
| 2019/0099125 A1* | 4/2019 | Schnall | A61B 5/4818 |

FOREIGN PATENT DOCUMENTS

| | | |
|---|---|---|
| WO | 2014197822 A2 | 12/2014 |
| WO | 2015092606 A1 | 6/2015 |
| WO | 2016186724 A1 | 11/2016 |
| WO | 2017212370 A1 | 12/2017 |

OTHER PUBLICATIONS

European Search Report from EP Application No. 18182957, Jan. 16, 2019.

Extended European Search Report issued in corresponding European Patent Application No. 23217439.1, mailed Jun. 18, 2024, 5 pages.

* cited by examiner

APPARATUS, SYSTEM AND METHOD FOR DIAGNOSING SLEEP

CROSS-REFERENCE TO RELATED APPLICATIONS

The present application claims priority to European Patent Application No. 18182957.3, filed on Jul. 11, 2018.

FIELD OF THE INVENTION

The present invention generally relates, amongst others, to a system for diagnosing sleep. More particular, it relates to the detection of sleep events by monitoring the peripheral arterial tone.

BACKGROUND OF THE INVENTION

Sleep diagnosis is a medical field wherein a patient's sleep is monitored during a certain time, e.g. one or more nights. Based on the monitoring, different sleep events may be identified such as for example apnoeic events, snoring or limb movements.

Sleep events may be determined by a polysomnography (PSG) during which different body functions are monitored such as the brain by electroencephalography (EEG), the eye movements by electrooculography (EOG), the muscle activity or skeletal muscle activation by electromyography (EMG), heart rhythm by electrocardiography (ECG), and respiratory airflow. Despite it being considered as the gold standard, this technique has several drawbacks. First, the test itself may require hospitalization or set-up of the test in the home environment by a healthcare professional. Second, the interpretation of the test is not fully automated, requiring a sleep technician to manually analyse the recorded signals thereby introducing inter-scorer variation and limiting the diagnostic accuracy. Third, the test may interfere with the person's sleep due to the complex wiring and overall overhead thereby influencing critical clinical parameters such as supine sleep time, sleep onset, arousals during sleep, and so forth. Forth, sleeping disorders such as sleep apnoea are known to have a high inter-night variability, and the current diagnostic systems are not suited for a multi-night study due the clinical shortcomings, lack of convenience, and high cost per examination.

EP0926980B1 discloses a solution that monitors changes in the peripheral arterial tone for detecting a change in the physiological condition of a patient, e.g. an apnoeic event. In EP0926980B1, the arterial tone is defined as the degree of "active tension" which the smooth muscle fibres surrounding the arteries impart. When activated (usually by sympathetic nerve endings or by blood borne or locally elaborated mediators), these fibres contract and in so doing reduce the calibre of the arteries. When the degree of active tension is high, this results in a state of vasoconstriction and conversely, when the degree of active tension is low vasodilation occurs. To this end, EP0926980B1 further discloses an apparatus for detecting such a change in the physiological condition of a patient comprising at least i) a probe to be applied to the distal end of the digit of the patient adapted to sense the peripheral arterial tone of the digit; and ii) a processor adapted to receive signals from the probe and to provide an output indicating changes in the peripheral arterial tone of the digit, thereby indicating a physiological state or medical condition of the patient. The probe further comprises a membrane for applying a static pressure field around the distal end of the digit of the patient, including the extreme digit tip of the distal end which static pressure field is sufficient to (a) substantially prevent venous pooling in said distal end, (b) substantially prevent uncontrolled venous backflow at said distal end, and (c) partially unload the wall tension of, but not to occlude, the arteries in said distal end when the digit is at heart level or below.

A disadvantage of the above solution is that the apparatus has many components, making it, although portable, still cumbersome to wear and expensive. Moreover, it is impractical due to the need for a probe to apply a static pressure field around the distal end of the digit of the patient for avoiding venous blood pooling. During use, the apparatus may therefore hinder the person and affect sleep quality or even sleep posture.

SUMMARY OF THE INVENTION

It is an object of the present invention to alleviate the above identified problems and to provide a solution for diagnosing sleep by the peripheral arterial tone that is easy to use, does not hinder the patient, and is cheap.

This object is achieved, according to a first aspect of the invention, by a system for diagnosing sleep comprising an apparatus configured to be attached to a patient; the apparatus comprising i) an optical sensor configured to measure a blood volume pulse of the patient; and ii) a wireless communication interface configured to wirelessly transmit the measured blood volume pulse. The system further comprises means for performing i) obtaining the wirelessly transmitted measured blood volume pulse; ii) deriving from the blood volume pulse the peripheral arterial tone; and iii) determining occurrences of sleep events from changes in the peripheral arterial tone.

The blood volume pulse is the output signal of the optical sensor and is characterized by the amount of light that is reflected or absorbed by a tissue. The apparatus does not perform any processing on the blood volume pulse but transmits it wirelessly for further processing by the remote means. In other words, the peripheral arterial tone nor the derived sleep events are determined by the apparatus but by the remote means. The wireless communication interface is preferably a low power communication interface, e.g. a Bluetooth Low Energy, BLE, wireless interface.

This way, the number of components in the apparatus are limited such that it can be made small, portable and does not interfere with the patient during the sleep diagnosis. As the actual processing of the blood volume pulse is performed remotely, the apparatus is very energy efficient. Therefore, the apparatus may be used for several nights in a row without recharging or swapping batteries. Furthermore, smaller batteries such as button cells may be used to further miniaturize the apparatus. The miniaturisation of the apparatus further allows for a simultaneous recording of sleep events and the provision of therapy, such as when it is incorporated into a positional therapy or mandibular advanced device, both being devices which may be used to treat sleep disordered breathing.

According to an embodiment, the apparatus is configured to be attached to the skin of the patient.

The apparatus may further comprise an adhesive for attaching the apparatus to the skin of the patient. Due to the lightweight and small construction, the apparatus can just stick to the skin without further means than the adhesive. There is thus no need for further straps or for further wiring to other components.

The apparatus may further be configured to be attached to at least one of the group consisting of a nostril, an ear, a forehead, a finger, inside a mouth, and a toe. Again, due to small size, the apparatus may be easily attached onto any of these locations without further disturbing the patient's sleep. The apparatus is thus not limited to be attached to a finger but may be used in locations which allows for a better signal reception due to the proximity of vascular beds causing the measurements site to be well perfused such as at the nostril, the ear or even inside the mouth, e.g. onto the gum or the cheek.

According to a preferred embodiment, the peripheral arterial tone is further determined by calculating an envelope of the blood volume pulse. In other words, the peripheral arterial tone is approximated by taking the envelope of the blood volume pulse. Experiments have shown that this approximation may be used for derivation of the various sleep events disclosed herein, either from the blood volume pules measurements alone or in combination with other physiological measurements.

A sleep event may for example comprise at least one of the group consisting of sleep disordered breathing events, periods of intense snoring, limb movements, cortical arousals, autonomic arousals, periods of bruxism, hypnic jerks, tossing events, and turning events.

Preferably, the optical sensor is a reflectance based optical sensor comprising a light emitter and a light sensor. Such a sensor is configured to measure the light reflected from the tissue. As both the light emitter and receptor are located on the same side of the tissue, the apparatus may again be further miniaturized. For example, all components of the apparatus may be located on a single circuit board.

More preferably the apparatus comprises a flat surface around the optical sensor This way, a uniform compression is achieved around the sensing area thereby avoiding venous blood pooling which could disturb the measurements. Furthermore, no further means for applying a static pressure field such as a probe around the finger are needed.

Advantageously, the system further comprises a wraparound configured to attach the apparatus against the skin of the patient. Such a wraparound may further aid to press the sensor area against the tissue. This further aids in obtaining the uniform compression, advantageously in combination with the flat surface, to avoid venous blood pooling. Furthermore, the wraparound does not peel off as may the case with an adhesive applied to the underside of the apparatus.

According to an embodiment, the optical sensor further comprises a light emitter, a light sensor and the apparatus further comprises means for performing:
  gradually increasing the light output of the light emitter;
  measuring the gradually increased light by the light sensor; and
  when the light sensor is saturated by the gradually increased light, configuring the light output of the light emitter below the saturation point of the light sensor thereby calibrating the optical sensor.

By the above steps, the sensor may be calibrated without performing any signal processing on the measured signal, i.e., there is no need to derive first a DC and AC component from the signal. Therefore, as the further signal components are of no use for the apparatus, further processing circuitry and additional energy consumption can be avoided. This allows for the further miniaturization of the apparatus.

The above calibration procedure may further be performed periodically, when detecting that light sensor is saturated or near saturation, and/or when detecting a significant drop in the measured light.

According to an embodiment, the means comprise a mobile communication device configured to receive the wirelessly transmitted measured blood volume pulse.

The mobile communication device is preferably located near the patient when in use allowing for a low power signal transmission. It may for example correspond to a mobile phone, a smartphone, a tablet computer or a laptop computer.

Advantageously, the mobile communication device is further configured to perform the deriving of the peripheral arterial tone and/or the determining of the sleep events. The mobile communication device may be further configured to wirelessly transmit the measured blood volume pulse to a remote service for performing the deriving and/or determining. This allows for a centralized cloud-based solution wherein the determining of the sleep events is done off-site. This further allows to combine measurements from different patients to further improve the determining of the sleep events.

The means may further comprise at least one processor and at least one memory including computer program code, the at least one memory and computer program code configured to, with the at least one processor, cause the performance of the controller.

According to a second aspect, the invention further relates to the apparatus of the system according to the first aspect.

According to a third aspect, the invention relates to a kit of parts comprising the apparatus according to the second aspect and the wraparound configured to attach the apparatus against the skin of the patient.

DETAILED DESCRIPTION OF EMBODIMENT(S)

Figure 1C:
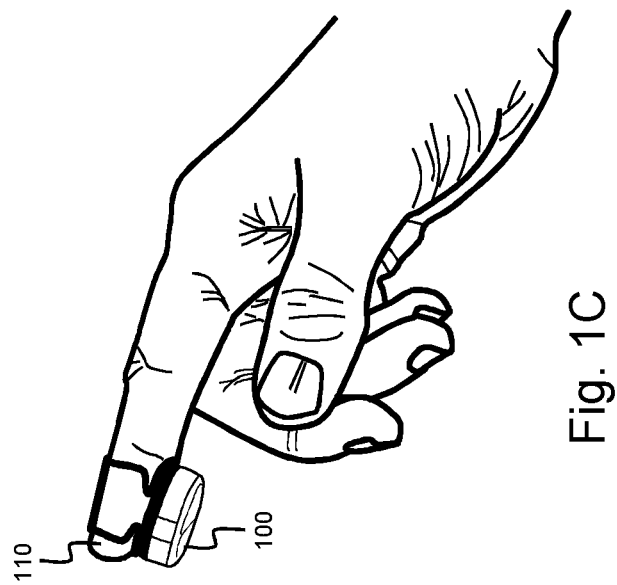
FIG. 1C illustrates the apparatus of FIGS. 1A and 1B when worn by a patient.
Figure 1A:
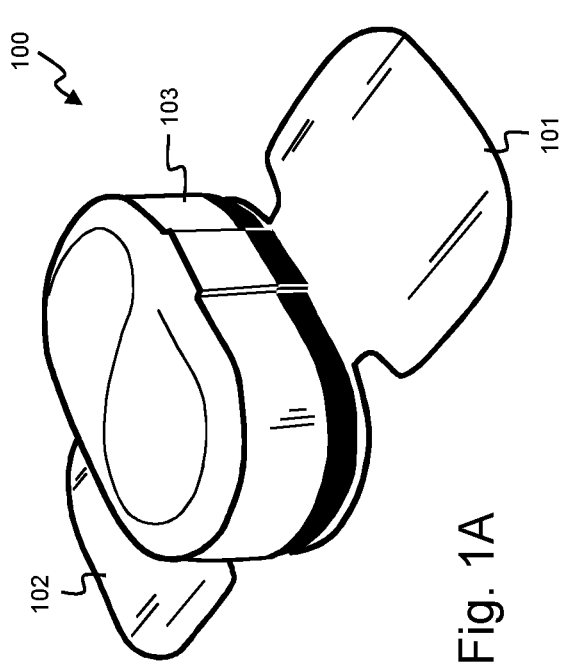
FIG. 1A illustrates a top side view of an apparatus for measuring a blood volume pulse according to an embodiment of the invention.
Figure 1B:
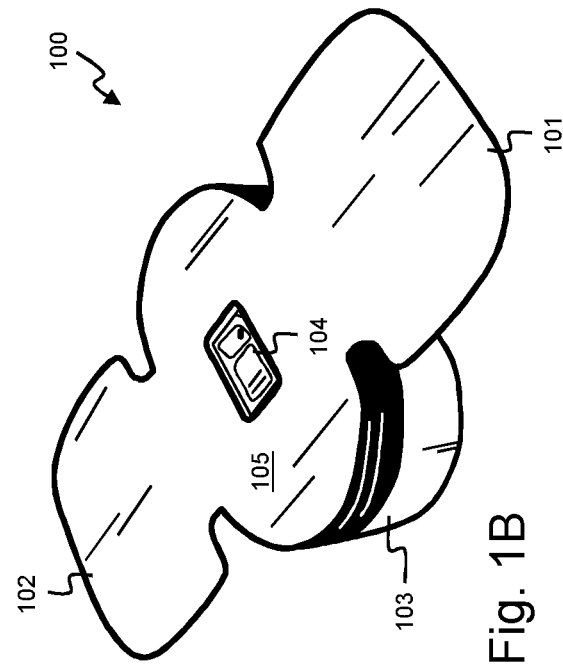
FIG. 1B illustrates a bottom side view of an apparatus for measuring a blood volume pulse according to an embodiment of the invention.

The present disclosure relates to a system for diagnosing sleep of a patient. By a sleep diagnosis, sleep disorders may be discovered and treated adequately. An embodiment of such a system will be further described with reference to FIGS. 1A, 1B, 2 and 3. FIGS. 1A, 1B and 1C illustrates an outside view of an apparatus 100 which is part of the system. The apparatus 100 is configured to be attached by one side 105 to a tissue of the patient, for example onto a fingertip 110. At the side 105, apparatus 100 comprises a reflectance based optical sensor 104. This sensor is configured to measure the blood volume pulse when attached to the patient. When attached, the sensor emits light onto the tissue of the patient and measures the reflected light. The so-measured signal is then indicative for the blood volume pulse in the tissue where the sensor is attached to.

Apparatus 100 may be dimensioned such that is sticks to the skin of the patient during use by an adhesive applied on the side 105. To further improve the adherence to the skin, apparatus 100 may further comprise flaps 101 having an adhesive layer.

Figure 8B:
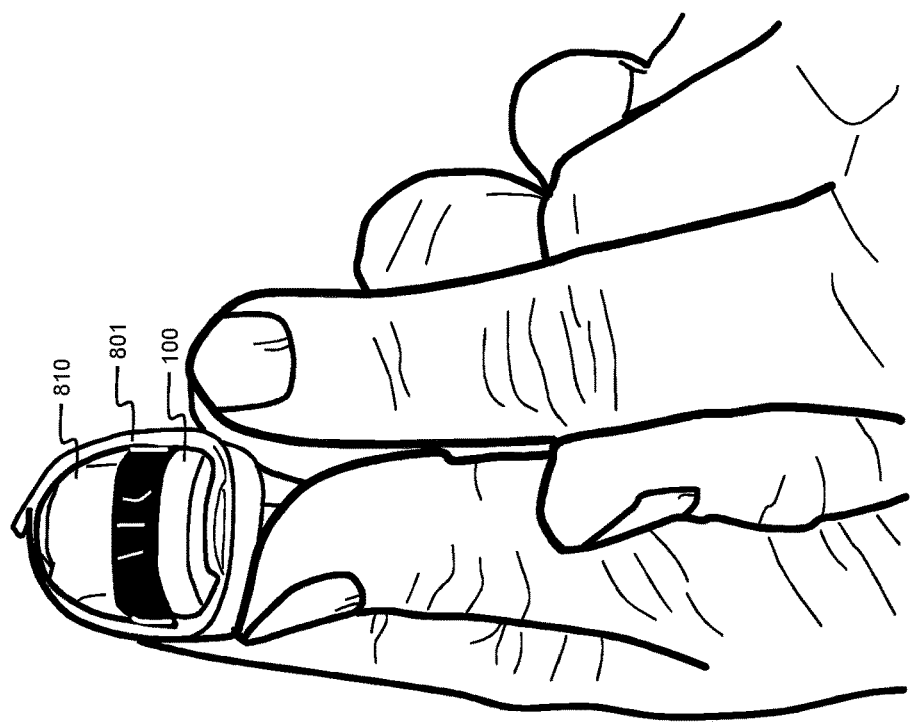
FIG. 8B illustrates the apparatus and wraparound of FIG. 8A when worn by a patient.
Figure 8A:
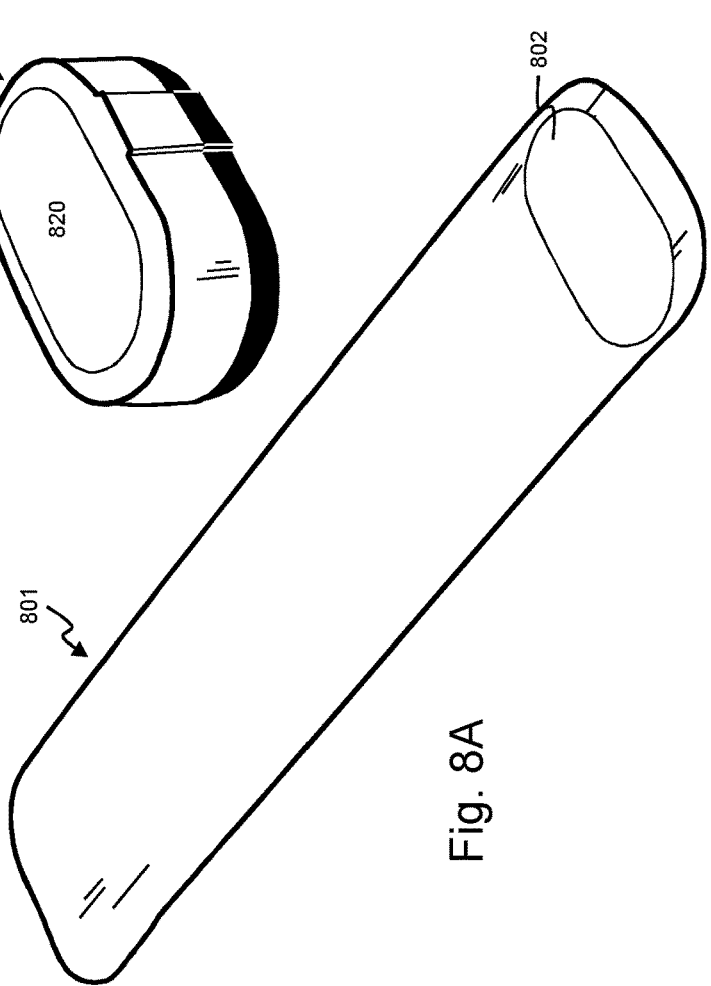
FIG. 8A illustrates a top side view of an apparatus for measuring a blood volume pulse and a wraparound according to an embodiment of the invention.

Alternatively, or complementary, as further illustrated in FIG. 8A and FIG. 8B, apparatus 100 may be attached to a finger 810 or a toe by a wraparound 801, i.e. by a means 801 for holding the apparatus 100 attached to the finger 810 wherein the means is configured to wrap around the finger 810 and apparatus 100 thereby holding the apparatus 100 against the finger 810. Wraparound 801 may comprise an adhesive on one side for sticking the wraparound 801 to the topside 820 of the apparatus 100 one the one side and for sticking the wraparound to the finger 810 and/or to the wraparound's 801 other side when in use. Wraparound 801 may further comprise a region 802 indicating the side of the wraparound which is to be attached to the topside 820 of the apparatus 100. By the wraparound, the sensor area 105 may be pushed or pressed against the skin thereby creating a uniform compression around the sensor are 104 which avoids venous blood pooling. The problem of blood pooling may be avoided without the need for pressure controlling circuitry such as for example an actively or passively pressurized membrane. By the wraparound 801, the adhesive is further protected against peeling off as may be the case when only an adhesive is applied on the apparatus 100 or the flaps 101.

The apparatus 100 may have a flat surface around the optical sensor at the side 105. The optical sensor 104 is further recessed with respect to this flat surface. This way, when the apparatus 100 is pressed against the tissue of the patient, an even more uniform compression is obtained further avoiding the venous blood pooling. Advantageously, the adhesive is applied on this flat surface to further aid the adherence of the apparatus to the skin. The flaps 101, 102 may further aid in applying the pressure and keeping the device in place.

Apparatus 100 may further be dimensioned such that the sensor may be attached to different kinds of tissue. For example, apparatus 100 may be attached onto different positions of the patient's skin including a nostril, an ear, the forehead, a finger and a toe. Alternatively, the apparatus may be attached to a soft tissue inside the patient's mouth such as to the gum or the cheek.

Figure 2:
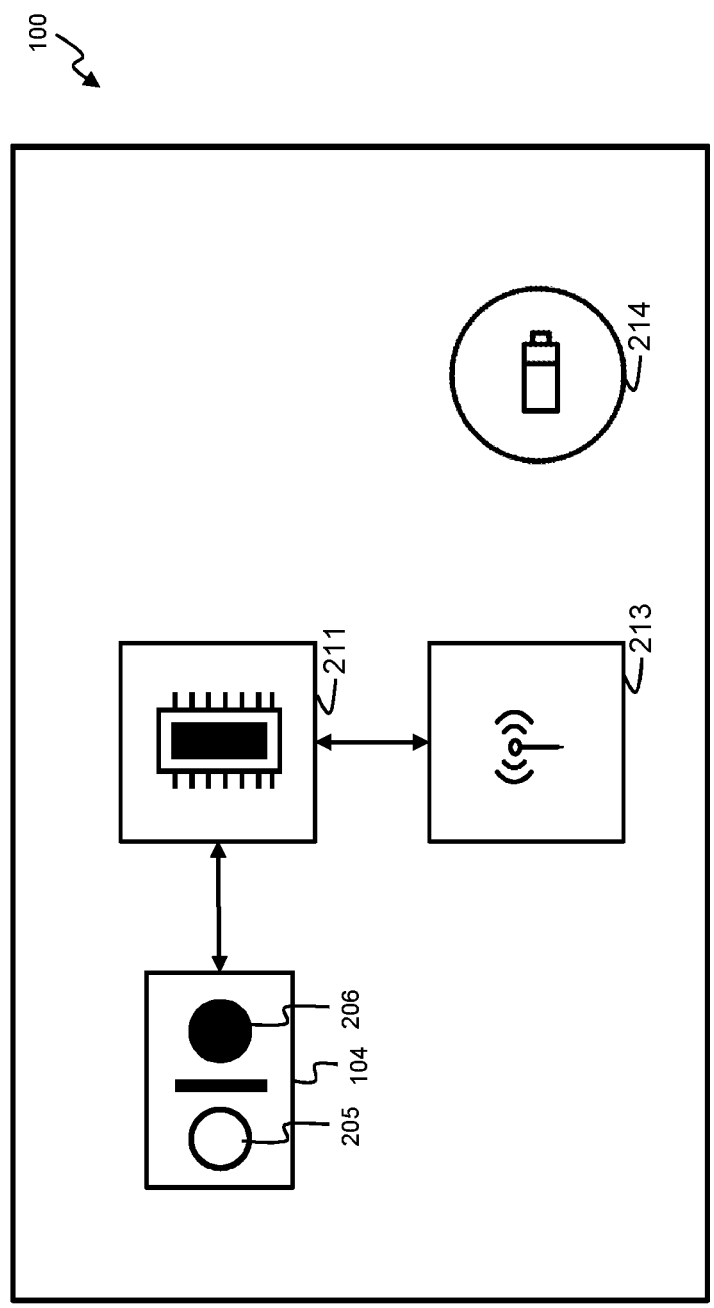
FIG. 2 illustrates components of an apparatus for measuring a blood volume pulse according to an embodiment of the invention.

FIG. 2 illustrates the different components of apparatus 100 for determining the blood volume pulse. Apparatus 100 comprises a battery 214 for powering the different electrical components 104, 211 and 213. As already described, apparatus 100 comprises a reflectance based optical sensor 104. Optical sensor 104 is powered by the battery 214, e.g. a button cell. Optical sensor 104 comprises a light emitter 205, e.g. a light emitting diode, for transmitting light into the attached tissue. Optical sensor 104 also comprises a light sensor for sensing the light transmitted by emitter 205 and reflected back onto the sensor 206. Sensor 206 may for example correspond to a photodiode.

Apparatus 100 further comprises control circuitry 211 for controlling the optical sensor 104, i.e., for enabling or disabling the sensor and for receiving the measured blood volume pulse values from the sensor 104. Control circuitry 211 may further comprise a memory component for temporarily storing the obtained measurements. Control circuitry 211 is further coupled to a wireless interfacing circuitry 213 and configured to forward the measurements to the wireless interfacing circuitry 213. Wireless interface 213 may support a short range and/or low power wireless communication protocol for efficient transmission of the measurements to a receiving part of the system. Wireless interface 213 may for example operate according to the Bluetooth Low Energy, BLE, protocol as defined by the Bluetooth Special Interest Group or according to a Near Field Communication, NFC, protocol. Operation by such protocols together with forwarding of the raw sensor 104 data allows miniaturization of apparatus 100 such that it fits on a finger or a nostril and allows operation during multiple nights.

Figure 3:
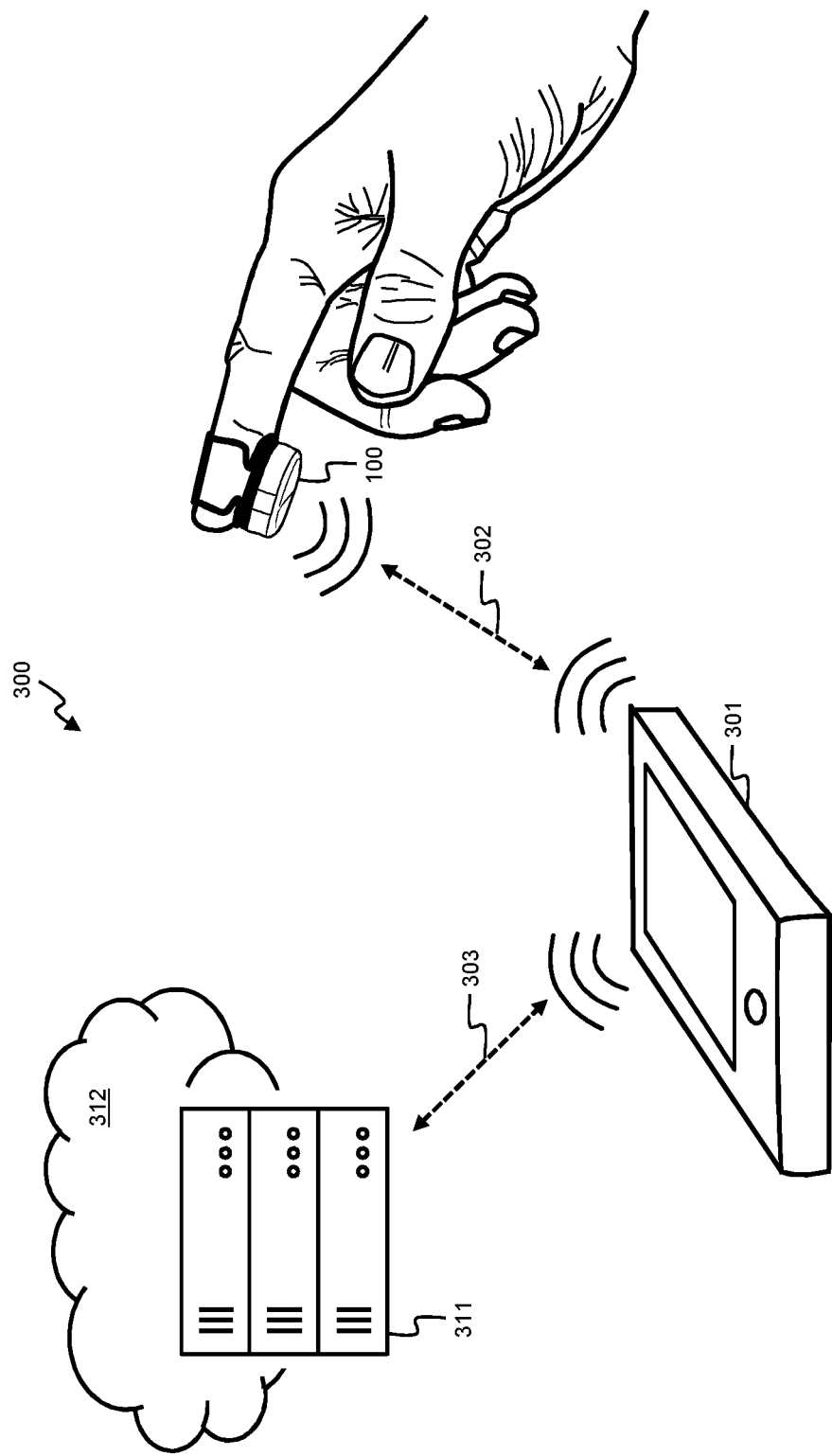
FIG. 3 illustrates a system for determining a sleep event according to an embodiment of the invention.

FIG. 3 illustrates a system 300 for diagnosing sleep of a patient according to an embodiment. System 300 comprises the apparatus 100 configured to measure and wirelessly transmit the blood volume pulse of the patient during sleep. System 300 further comprises a mobile communication device 301 further configured to receive the blood volume pulse measurements transmitted by apparatus 100. Apparatus 100 and device 301 may be configured to exchange the blood volume pulse measurements in a continuous manner or in a periodic manner. In the latter case, apparatus 100 stores the measurements during a certain time windows and the transmits the stored measurement in batch to the mobile device 301.

Figure 4:
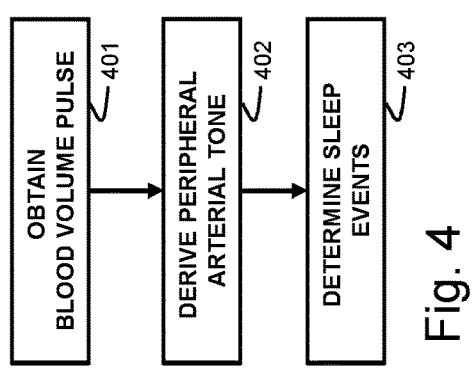
FIG. 4 illustrates steps performed for diagnosing sleep according to an embodiment of the invention.

FIG. 4 illustrates further steps performed by the system 300 for diagnosing the sleep of the patient based on the obtained blood volume measurements wherein the first step 401 is the obtaining of these measurements. The following steps may be performed by any suitable computing system. The steps may for example all be performed on mobile device 301. Alternatively, mobile device 301 may forward the blood volume measurements to another remote computing system 311 which on its turn performs the further steps. Remote computing system 311 may correspond to a remote cloud-based computing service accessible over the Internet or over a private network. The steps may also be partly performed on device 301 and partly on the remote computing system 311.

Figure 7A:
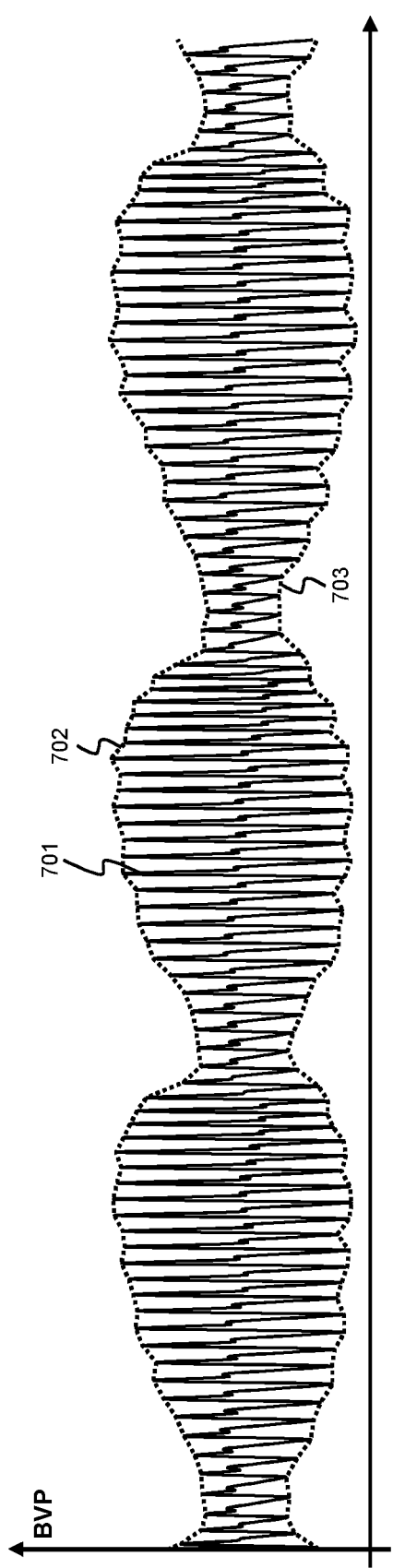
FIG. 7A shows a plot of a measured blood volume pulse, BVP, as a function of time and the envelope of the measured BVP.
Figure 7B:
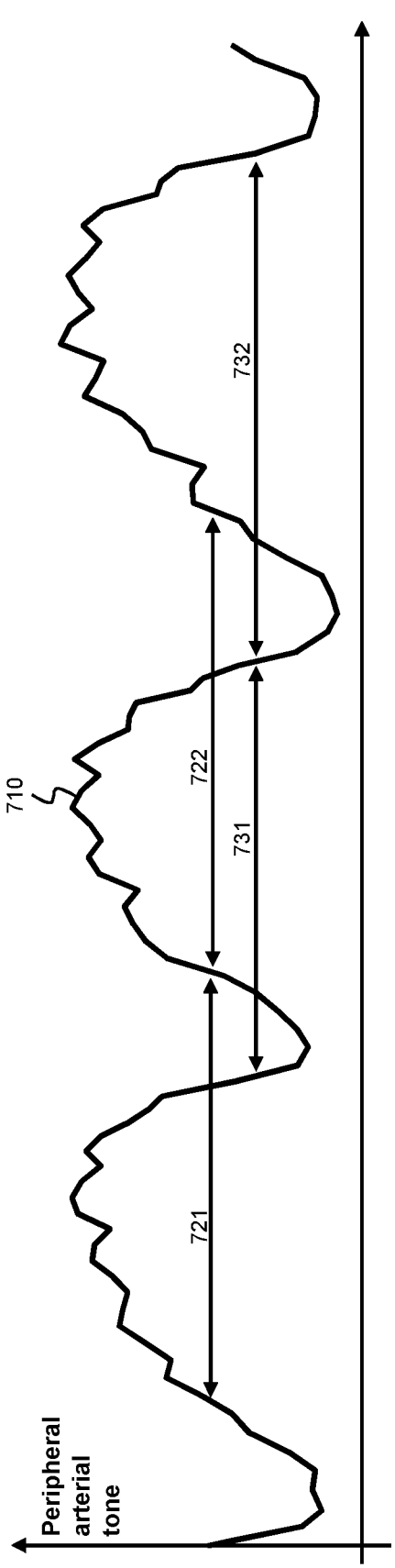
FIG. 7B shows a plot of a peripheral arterial tone as a function of time obtained from the blood volume pulse shown in FIG. 7A.

In step 402 the peripheral arterial tone is derived from the measured blood volume pulse. This may be done by deriving the envelope of the obtained blood volume pulse measurements. This process is illustrated in FIG. 7A and FIG. 7B. In FIG. 7A the measured blood volume pulse 701 is shown on the vertical axis as a function of time according to the horizontal axis. In step 402, the upper envelope 702 and lower envelope 703 of the BVP 701 is determined. As the BVP 701 is an oscillating signal with a periodicity determined by the hearth beat of the patient, the upper envelope 702 is determined as a smooth curve outlining the upper extremities of the BVP 701 and the lower envelope 703 is determined by the lower extremities of the BVP 701. The difference between the upper and lower envelopes 702 and 703 is then indicative for the peripheral arterial tone 710 as illustrated in FIG. 7B.

In the next step 403, one or more sleep events are determined by inspecting the changes in the peripheral arterial tone 710, e.g. by inspecting the decrease 731, 732 in the amplitude of the peripheral arterial tone and/or the increase 721, 722 in the amplitude of the peripheral arterial tone, optionally in combination with the measured BVP 702. A sleep event may for example comprise a sleep disordered breathing events such as apnoeic events, periods of intense snoring, limb movements either as periodic or single events, cortical arousals, autonomic arousals, periods of bruxism, hypnic jerks, tossing events, and turning events. For example, an apnoeic event may be determined by considering the temporal proximity of a peripheral arterial tone amplitude decrease 731, 732, a blood oxygen desaturation, and a decrease of the inter pulse interval of the blood volume pulse. An autonomic arousal may be determined by considering the temporal proximity of a peripheral arterial tone amplitude decrease 731, 732 and a decrease of the inter-pulse-interval of the blood volume pulse. A bruxism event may be determined by the temporal proximity of a peripheral arterial tone amplitude decrease 731, 732 and a decrease of the inter-pulse-interval of the blood volume pulse, under the absence of limb movement. A periodic limb movement event may be determined by the temporal proximity of a peripheral arterial tone amplitude decrease 731, 732 and a decrease of the inter-pulse-interval of the blood volume pulse, under the presence of limb movement.

Figure 6:
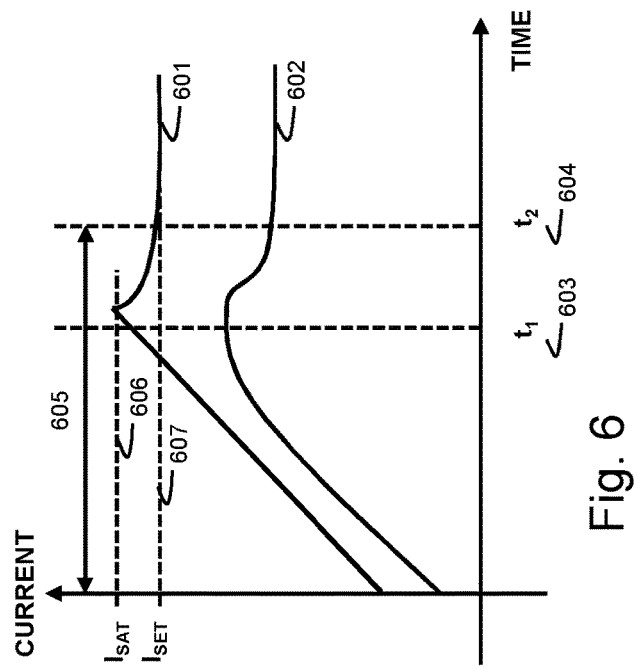
FIG. 6 illustrates steps performed by an apparatus for calibrating an optical sensor.

FIG. 6 illustrates steps performed by control circuitry 211 of apparatus 100 for calibrating the optical sensor 104, more specifically for determining the optimal light output of the light emitter 205 of the apparatus 100. To this end, apparatus 100 may perform a calibration cycle 605 from time to time, e.g. when the apparatus 100 has been attached to the tissue of the patient before going to sleep. FIG. 6 illustrates the current 601 to the light emitter 205 as a function of time and the current 602 received by the light sensor 206 as a function of time. The current 601 is a direct representation of the light output of the light emitter 205 and the current 602 is a direct representation of the light received by the sensor 206. Typically, the higher the light output of the emitter, the higher the signal to noise ratio of the sensor 206 as long as the sensor 206 does not saturate. During a first time interval 605, the current 601 to the light emitter is gradually increased while the current 602 from the light sensor 206 is constantly measured. At a certain point in time 603, the light sensor 206 is saturated and, therefore, its output current 602 stagnates. This point in time 603 determines the saturation current 606 for the light emitter 205. Thereupon, the current 601 is decreased below this saturation current 606 up to a working point current 607. This decrease may be relative, e.g. by between 5% and 10%, or may be absolute. After the working point of the emitter 205 is set, the calibration phase ends at time 604 and normal operation of the apparatus 100 resumes. Control circuitry 211 may further be configured to reperform the calibration upon certain calibration triggering events. A first calibration event may be the expiration of a timer such the calibration is performed periodically. A second calibration event may be the detection of a saturation of the light sensor 206 during normal operation, e.g. by detecting the saturation point 603 during normal operation. A third calibration event may be when a significant drop in the measured light is detected. Such drop may cause a decrease in signal quality and be due to a position switch of the patient, causing the light sensor to move relative to the skin or tissue which may further create an airgap between sensor and skin.

Figure 5:
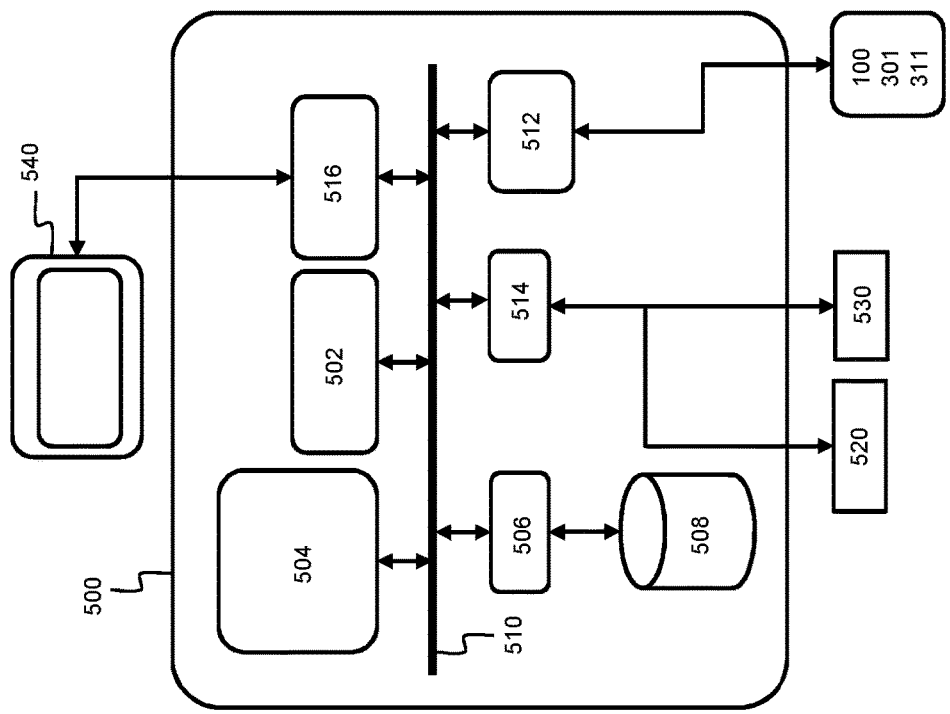
FIG. 5 illustrates a computing system suitable for performing steps according to various embodiments of the invention.

FIG. 5 shows a suitable computing system 500 for implementing the steps with reference to FIG. 4. Computing system 500 may in general be formed as a suitable general-purpose computer and comprise a bus 510, a processor 502, a local memory 504, one or more optional input interfaces 514, one or more optional output interfaces 516, a communication interface 512, a storage element interface 506, and one or more storage elements 508. Bus 510 may comprise one or more conductors that permit communication among the components of the computing system 500. Processor 502 may include any type of conventional processor or microprocessor that interprets and executes programming instructions. Local memory 504 may include a random-access memory (RAM) or another type of dynamic storage device that stores information and instructions for execution by processor 502 and/or a read only memory (ROM) or another type of static storage device that stores static information and instructions for use by processor 502. Input interface 514 may comprise one or more conventional mechanisms that permit an operator or user to input information to the computing device 500, such as a keyboard 520, a mouse 530, a pen, voice recognition and/or biometric mechanisms, a camera, etc. Output interface 516 may comprise one or more conventional mechanisms that output information to the operator or user, such as a display 540, etc. Communication interface 512 may comprise any transceiver-like mechanism such as for example one or more Ethernet interfaces that enables computing system 500 to communicate with other devices and/or systems, for example with other apparatus 100, mobile device 301 or computing system 311. The communication interface 512 of computing system 500 may be connected to such another computing system by means of a local area network (LAN) or a wide area network (WAN) such as for example the internet. Storage element interface 506 may comprise a storage interface such as for example a Serial Advanced Technology Attachment (SATA) interface or a Small Computer System Interface (SCSI) for connecting bus 510 to one or more storage elements 508, such as one or more local disks, for example SATA disk drives, and control the reading and writing of data to and/or from these storage elements 508. Although the storage element(s) 508 above is/are described as a local disk, in general any other suitable computer-readable media such as a removable magnetic disk, optical storage media such as a CD or DVD, -ROM disk, solid state drives, flash memory cards, . . . could be used. Computing system 500 may thus correspond to or be part of mobile communication device 301 or remote computing system 311.

As used in this application, the term "circuitry" may refer to one or more or all of the following:
  (a) hardware-only circuit implementations such as implementations in only analog and/or digital circuitry and
  (b) combinations of hardware circuits and software, such as (as applicable):
    (i) a combination of analog and/or digital hardware circuit(s) with software/firmware and
    (ii) any portions of hardware processor(s) with software (including digital signal processor(s)), software, and memory(ies) that work together to cause an apparatus, such as a mobile phone or server, to perform various functions) and
  (c) hardware circuit(s) and/or processor(s), such as microprocessor(s) or a portion of a microprocessor(s), that requires software (e.g. firmware) for operation, but the software may not be present when it is not needed for operation.

This definition of circuitry applies to all uses of this term in this application, including in any claims. As a further example, as used in this application, the term circuitry also covers an implementation of merely a hardware circuit or processor (or multiple processors) or portion of a hardware circuit or processor and its (or their) accompanying software and/or firmware. The term circuitry also covers, for example and if applicable to the particular claim element, a baseband integrated circuit or processor integrated circuit for a mobile device or a similar integrated circuit in a server, a cellular network device, or other computing or network device.

Although the present invention has been illustrated by reference to specific embodiments, it will be apparent to those skilled in the art that the invention is not limited to the details of the foregoing illustrative embodiments, and that the present invention may be embodied with various changes and modifications without departing from the scope thereof. The present embodiments are therefore to be considered in all respects as illustrative and not restrictive, the scope of the invention being indicated by the appended claims rather than by the foregoing description, and all changes which come within the scope of the claims are therefore intended to be embraced therein.

It will furthermore be understood by the reader of this patent application that the words "comprising" or "comprise" do not exclude other elements or steps, that the words "a" or "an" do not exclude a plurality, and that a single element, such as a computer system, a processor, or another integrated unit may fulfil the functions of several means recited in the claims. Any reference signs in the claims shall not be construed as limiting the respective claims concerned. The terms "first", "second", third", "a", "b", "c", and the like, when used in the description or in the claims are introduced to distinguish between similar elements or steps and are not necessarily describing a sequential or chronological order. Similarly, the terms "top", "bottom", "over", "under", and the like are introduced for descriptive purposes and not necessarily to denote relative positions. It is to be understood that the terms so used are interchangeable under appropriate circumstances and embodiments of the invention are capable of operating according to the present invention in other sequences, or in orientations different from the one(s) described or illustrated above.

The invention claimed is:

1. A system configured to diagnose sleep comprising an apparatus configured to be attached to a patient, the apparatus comprising:
    an optical sensor configured to measure a blood volume pulse of the patient;
    a wireless communication interface configured to wirelessly transmit data representing the measured blood volume pulse; and
    wherein the system further comprises one or more processors configured to:
        obtain the wirelessly transmitted data representing the measured blood volume pulse;
        derive, by processing the data representing the measured blood volume pulse, a signal that represents peripheral arterial tone, wherein the derivation comprises:
            determining an upper envelope of the measured blood volume pulse and a lower envelope of the measured blood volume pulse, wherein the upper envelope is a smoothed curve connecting peaks of the measured blood volume pulse and the lower envelope is a smoothed curve connecting troughs of the measured blood volume pulse, and
            calculating the signal that represents peripheral arterial tone based on a difference between the upper envelope and the lower envelope; and
        determine occurrences of sleep events from changes in the derived peripheral arterial tone signal,
        diagnose the sleep of the patient based on the determined occurrences of sleep events.

2. The system according to claim 1 wherein the apparatus is configured to be attached to a portion of skin of the patient.

3. The system according to claim 2, wherein the apparatus further comprises an adhesive for attaching the apparatus to the skin of the patient.

4. The system according to claim 2, further comprising a wraparound configured to attach the apparatus against the skin of the patient.

5. The system according to claim 1, wherein the apparatus is configured to be attached to at least one of the group consisting of a nostril, an ear, a forehead, a finger, inside a mouth, and a toe.

6. The system according to claim 1, wherein a sleep event comprises at least one of the group consisting of sleep disordered breathing events, periods of intense snoring, limb movements, cortical arousals, autonomic arousals, periods of bruxism, hypnic jerks, tossing events, and turning events.

7. The system according to claim 1, wherein the optical sensor is a reflectance based optical sensor comprising a light emitter and a light sensor.

8. The system according to claim 7, wherein the apparatus comprises control circuitry configured to:
    gradually increase light output of the light emitter;
    measure the gradually increased light by the light sensor; and
    when the light sensor is saturated by the gradually increased light, configure the light output of the light emitter below the saturation point of the light sensor thereby calibrating the optical sensor.

9. The system according to claim 1, further comprising a mobile communication device, wherein the mobile communication device comprises a processor of the one or more processors, and wherein the mobile communication device is configured to receive the wirelessly transmitted data representing the measured blood volume pulse.

10. The system according to claim 9, wherein the mobile communication device is further configured to perform the determination of the occurrences of sleep events.

11. The system according to claim 9, wherein the mobile communication device is further configured to wirelessly transmit the data representing the measured blood volume pulse to a remote service for performing the determination of the occurrences of sleep events.

12. The system according to claim 1, wherein the apparatus comprises a flat surface around the optical sensor.

13. The system according to claim 1, further comprising control circuitry that comprises a processor of the one or more processors and at least one memory including computer program code, the at least one memory and computer program code configured to, with the processor, cause operation of the control circuitry, the operation comprising the derivation of the signal representing the peripheral arterial tone.

14. The system according to claim 1, wherein, to determine occurrences of sleep events, the system is configured to detect a temporal proximity of a plurality of events, the plurality of events comprising first and second changes in the signal representing the peripheral arterial tone.

15. The system according to claim 14, wherein at least one of the first and second changes comprises amplitude decreases.

16. The system according to claim 14, wherein the second change comprises a subsequent corresponding change to the first change.

17. The system according to claim 14, wherein the first change and the second change comprise amplitude decreases.

18. The system according to claim 1, wherein the wireless communication interface is configured in a housing and is configured to transmit the data representing the measured blood volume pulse according to a Near Field Communication protocol or a Bluetooth protocol.

19. The system according to claim 18, wherein the housing is configured to be wearable on the patient.

20. The system according to claim 19, wherein the wireless communication interface and the optical sensor are powered by a battery within the housing.

21. The system according to claim 20, wherein the wireless communication interface and the optical sensor are within the housing, and the housing is configured to be wearable on a fingertip of the patient.

* * * * *